United States Patent [19]

Palmer

[11] Patent Number: 5,008,433
[45] Date of Patent: Apr. 16, 1991

[54] 2-HYDROXY-3-(4-METHOXYPHENYL)-3-(2-AMINOPHENYLTHIO)PROPIONIC ACID, 8'-PHENYLMENTHYL ESTER, ESPECIALLY FOR DILTIAZEM

[75] Inventor: James T. Palmer, Livermore, Calif.

[73] Assignee: Marion Laboratories, Inc., Kansas City, Mo.

[21] Appl. No.: 505,493

[22] Filed: Apr. 6, 1990

Related U.S. Application Data

[62] Division of Ser. No. 195,708, May 18, 1988.

[51] Int. Cl.$^5$ ............................................. C07C 323/36
[52] U.S. Cl. ...................................... 560/17; 540/491; 562/401; 562/431
[58] Field of Search .................. 560/17; 562/431, 401; 540/491

[56] References Cited

U.S. PATENT DOCUMENTS

| | | | |
|---|---|---|---|
| 3,562,257 | 2/1971 | Kugita et al. | 540/491 |
| 4,416,819 | 11/1983 | Nagao et al. | 540/491 |
| 4,587,242 | 5/1986 | Manghisi | 514/211 |

FOREIGN PATENT DOCUMENTS 53-018038  6/1978  Japan.
63-268663  11/1988  Japan.

OTHER PUBLICATIONS

Ort, O., *Organic Synthesis*, vol. 65, pp. 203–213 (1987).
Corey & Ensley, *Journal of American Chemical Society*, vol. 97, No. 23, pp. 6908–6909 (1975).
Oppolzer et al., *Helv. Chim. Acta*, 64, pp. 2802–2807 (1981).
Oppolzer et al., *Helv. Chem. Acta*, 64, pp. 2808–2811 (1981).
Whitesell et al., *J. Chem. Soc.*, Chem. Commun., pp. 988–989 (1982).
Whitesell et al., *J. Chem. Soc.*, Chem. Commun., pp. 989–990 (1982).

Primary Examiner—Jose G. Dees
Assistant Examiner—Vera C. Clarke
Attorney, Agent, or Firm—Michael B. Hurd

[57] ABSTRACT

The titled ester, especially having the (2S,3S)-configuration, which is an intermediate for the production of diltiazem, is provided. Very high yields are obtainable.

2 Claims, No Drawings

2-HYDROXY-3-(4-METHOXYPHENYL)-3-(2-AMINOPHENYLTHIO)PROPIONIC ACID, 8'-PHENYLMENTHYL ESTER, ESPECIALLY FOR DILTIAZEM

This is a division of application Ser. No. 07/195,708 filed May 18, 1988.

FIELD

This invention concerns such an optically active compound as a 2-hydroxy-3-(4-methoxyphenyl)-3-(2-aminophenylthio)propionic acid ester as one having optical activity not only due to chirality of the 2- and 3-carbons of the propionic chain but also due to such a chiral auxiliary as in the titled ester, with methods therefor and therewith. The ester is useful as a chemical intermediate, and in its (2S, 3S)-configuration as an intermediate for diltiazem, and so forth.

BACKGROUND

Kugita et al., U.S. Pat. No. 3,562,257 (Feb. 9, 1971), describes benzothiazepine derivatives, which are useful as antidepressants, tranquilizers and coronary vasodilators. Among these, diltiazem, i.e., 3-(acetyloxy)-5-[2-dimethylamino)ethyl]-2,3-dihydro-2-(4-methoxyphenyl)-1,5-benzothiazepin-4(5H)-one, is a well-known successful cardiac drug having calcium blocking activity. Vasodilating action is specific for the d-cis-isomer. The hydrochloride is often administered as, e.g., Cardizem ®.

As might be expected, various processes or methods for preparing such a benzothiazepine as diltiazem and its salts are generally further known. To permit isolation of the desired optically active isomer many of such methods include at least one resolution step.

Sanada et al., Jpn. Discl. No. 268663-1988 (Nov. 28, 1986), discloses (2R, 3S)-2,3-epoxy-3-(4-lower alkoxyphenyl)-propionic acid (−)-menthyl ester which is permitted to react with 2-aminothiophenol to produce 2(S)-hydroxy-3(S)-(4-lower alkoxyphenyl)-3-(2-aminophenylthio)propionic acid (−)-menthyl ester. Purportedly after hydrolysis, the acid product may be used to prepare corresponding 1,5-benzothiazepine derivatives, e.g., diltiazem hydrochloride.

SUMMARY

In general, this invention provides, in one aspect, methods comprising steps of: contacting, or reaction of (a) 4-methoxybenzaldehyde with (*)-8-phenylmenthyl chloroacetate, forming (2*, 3*)-3-(4-methoxyphenyl)glycidic acid, (*)-8'-phenylmenthyl ester; (b) contacting the composition of the first step (a), or reaction of the product from (a) with 2-aminothiophenol, such that a (2*, 3*)-2-hydroxy-3-(4-methoxyphenyl)-3-(2-aminophenylthio)propionic acid, (*)-8'-phenylmenthyl ester is prepared. Other aspects include further processing of said propionic acid (*)-8'-phenylmenthyl ester, to include room cold, or higher, e.g., 65° C., temperature hydrolyses, etc. Another aspect is a composition of matter comprising a (2*, 3*)-2-hydroxy-3-(4-methoxyphenyl)-3-(2-aminophenylthio)propionic acid, (*)-8'-phenylmenthyl ester.

Said glycidic acid and propionic acid (*)-8'-phenylmenthyl esters are useful as chemical intermediates, especially in their (2S, 3S)-configuration as intermediates for diltiazem, and so forth. The method(s) of preparation of said glycidic acid and/or propionic acid (*)-8'-phenylmenthyl ester(s) can be highly efficient, and thus, a method employing said (*)-8'-phenylmenthyl ester(s), for preparing corresponding 1,5-benzothiazepinones, in particular diltiazem and/or its pharmaceutically acceptable salts to include its hydrochloride, can be highly efficient as well.

ILLUSTRATIVE DETAIL

The (2*, 3*)-3-(4-methoxyphenyl)glycidic acid, (*)-8'-phenylmenthyl esters and the (2*, 3*)-2-hydroxy-3-(4-methoxyphenyl)-3-(2-aminophenylthio)propionic acid, (*)-8'-phenylmenthyl esters in this invention have a measure of optical activity both due to the 2- and 3-chiral carbons of the glycidic acid or propionic acid backbones and due to the 8'-phenylmenthyl chiral auxiliary. This is indicated by the notations "(2*, 3*)" and "(*)" in the nomenclature of this invention. Preferably, these esters correspond to the (2S, 3S)-configuration and (−)8'-phenylmenthyl esters. The (2*, 3*)-2-hydroxy-3-(4-methoxyphenyl)glycidic acid, (*)-8'-phenylmenthyl ester can be prepared by the reactions of p-anisaldehyde, with (*)-8-phenylmenthyl chloroacetate in the presence of a suitable base. The (2*, 3*)-2-hydroxy-3-(4-methoxyphenyl)-3-(2-aminophenylthio)-propionic acid (*)-8'-phenylmenthyl esters can be prepared by the reaction of 2-aminothiophenol with the corresponding reaction product of the first step. Steps and conditions are those sufficient to prepare the desired product. The following general reaction sequences fall within the spirit of this invention.

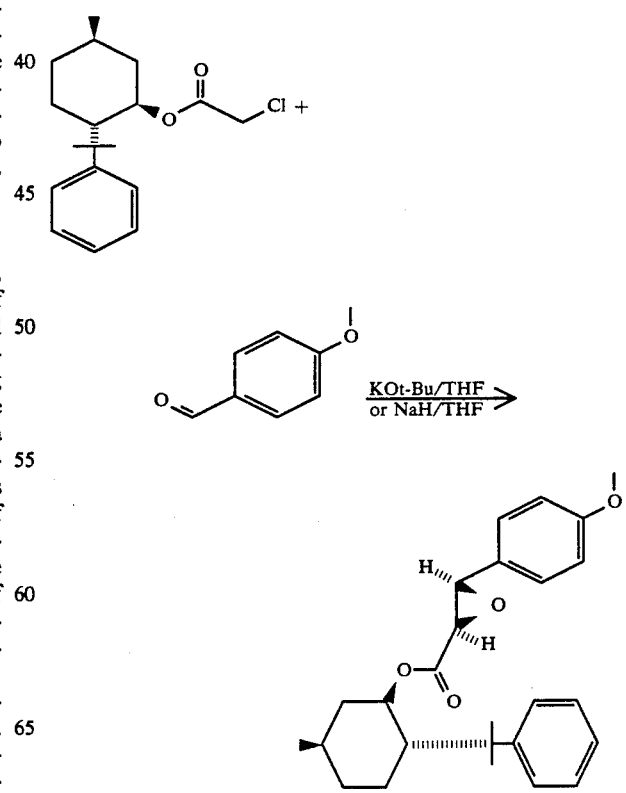

-continued

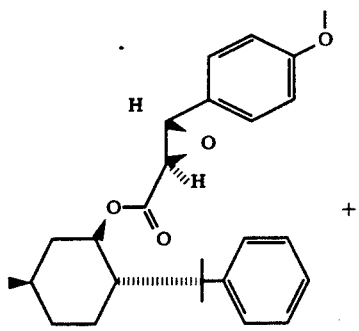

+

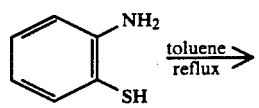

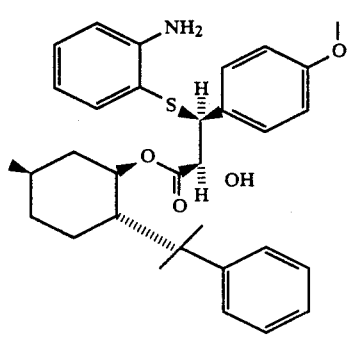

In general, a suitable solvent is employed. Although toluene and xylenes are operable reaction media for the first step, the preferred solvent is tetrahydrofuran (THF) because of the high yields which can be afforded thereby.

The Darzens-type reaction is best carried out slowly. Suitably slow rates of base addition include from 1/5 to 1 equivalent of base being added per hour, preferably about ½ equivalent per hour.

Concentrations of the reactants in the medium are desirably dilute. Suitable dilute concentrations of the reactants include from 0.02 molar (M) to 0.2M, preferably about 0.05M.

Temperatures of the glycidic acid 8'-phenylmenthyl ester product-forming step of this invention have some latitude. Suitable temperatures include from −20° C. to 30° C., preferably from −5° C. to 5° C.

Suitable bases include alkali metal hydrides and alkoxides. Amounts of the base may vary, suitable levels including from 1 eq. to 1.5 eq. with respect to other reactants.

The starting materials of this invention can be obtained or can be made by known methods or by methods analogous thereto. For example, the 4-methoxybenzaldehyde and chloroacetic acid and so forth can be obtained commercially. The (*)-8'-phenylmenthyl precursors, i.e., (*)-8-phenylmenthols can be obtained, or can be prepared by either the method of O. Ort, *Organic Syntheses*, Vol. 65, pp. 203-13 (1987), for (−)-8-phenylmenthol, or as referenced in E. J. Corey & H. E. Ensley, *Journal of the American Chemical Society*, Vol. 97, No. 23, pp. 6908-9 (1975), for (+)-8-phenylmenthol.

The (2*, 3*)-2-hydroxy-3-(4-methoxyphenyl)-3-(2-aminophenylthio)propionic acid, (*)-8'-phenylmenthyl esters are useful chemical intermediates. The (2S, 3S)-isomer in particular has utility for preparing such 1,5-benzothiazepine compounds as diltiazem and its pharmaceutically acceptable salts. Known methodology may be employed. For example, the (2S, 3S)-isomer ester can be hydrolyzed to the corresponding amino acid; the amino acid can be cyclized, and the resulting lactam can be N-alkylated and acetylated appropriately to obtain diltiazem, which may be converted to its pharmaceutically acceptable salts, e.g., its hydrochloride, by known methods. The following general reaction sequence falls within the spirit of this invention, which is also illustrated for the sake of conciseness to the cyclization stage only.

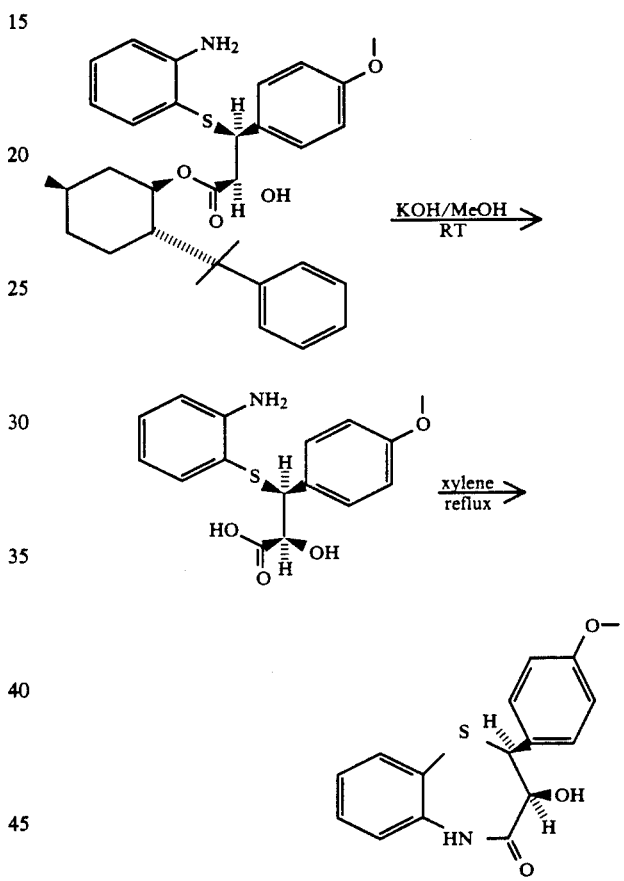

However, as generally indicated within the immediately foregoing sequence, hydrolysis of the 8'-phenylmenthyl ester of this invention is preferably performed at or near room temperature. Yields of corresponding acid thereby can be significantly greater than those obtained by performing the reaction at 65° C. or greater. Cold temperature hydrolysis may be employed.

Yields of the (2*, 3*)-2-hydroxy-3-(4-methoxyphenyl)-3-(2-aminophenylthio)propionic acid, (*)-8'-phenylmenthyl esters can be very high. The yields can be thus greater than 50–60% from p-anisaldehyde; the yields may depend primarily on the base employed.

The following examples further illustrate this invention.

EXAMPLE 1

A mixture of p-anisaldehyde (0.63 mL, 5.18 mmol) and (−)8-phenylmenthylchloroacetate (1.60 g, 5.18 mmol) was dissolved in THF (20 mL) and cooled to 0° C. in an ice/water bath. From an addition funnel equipped with needle valve, a solution of potassium t-butoxide (3.20 mL of saturated THF solution, diluted with 10 mL of THF, total volume 13.2 mL) was added very slowly (1 drop/5 sec). After 2 hours, the reaction was complete at addition of the last drop. The solvent was evaporated, the gummy residue was dissolved in ethyl acetate (100 mL), filtered through Florisil, and evaporated to dryness to yield 2.10 g of an oily residue, which was taken directly to the next step in the sequence.

To a solution of the Darzens product (2.10 g, at maximum 5.14 mmol) in 25 mL of toluene at room temperature was added 2-aminothiophenol (0.55 mL, 5.14 mmol). The mixture was heated at reflux overnight. The solution was then allowed to cool to room temperature, diluted with 1:1 ether/ethyl acetate (100 mL), washed successively with 1M HCl (2×25 mL), water (25 mL) and brine (25 mL), dried over sodium sulfate, filtered and evaporated. TLC (methylene chloride) showed good separation between the desired product and the undesired diastereomer. The residue was chromatographed on silica (70–200 mesh) using methylene chloride as eluent, followed by 4% ethyl acetate in methylene chloride to obtain the lower Rf isomer, if so desired. Following removal of solvents, there was obtained 1.62 g of (2S, 3S)-2-hydroxy-3-(4-methoxyphenyl)-3-(2-aminophenylthio)propionic acid, (−)-8′-phenylmenthyl ester (58.8% from p-anisaldehyde) and 0.37 g of the undesired diastereomer (14%). NMR data for the desired product (CDCl$_3$ solvent): 6.45–7.27 ppm (m, 13H); 4.86–4.96 ppm (dt, 1H); 4.23 ppm (d, 1H); 4.03 ppm (d, 1H); 3.74 ppm (s, 3H); 0.85–2.21 ppm (m, 17H).

EXAMPLE 2

To a mixture of (−)-8-phenylmenthylchloroacetate (1.68 g, 5.44 mmol) and p-anisaldehyde (0.657 mL, 5.44 mmol) in 25 mL of THF was added 60% sodium hydride in mineral oil (0.239 g, 5.98 mmol). The flask was immersed in a 40° C. water bath. After 3 hours, another 70 mg of sodium hydride were added. After 8 hours and a total of 1.5 equivalents of sodium hydride added, the reaction was quenched by means of slow addition of an equal volume of saturated aqueous ammonium chloride, with agitation and cooling, followed by addition of 20 mL water. The resulting solution was extracted twice with 50 mL portions of diethyl ether. The extracts were combined and dried over sodium sulfate and evaporated under reduced pressure to an oily residue.

The residue was dissolved in toluene (25 mL) and was treated with 1 equivalent of 2-aminothiophenol at reflux overnight. The solvent was evaporated and the residue was dissolved in ethyl ether (100 mL), washed with 1M HCl (2×50 mL), saturated sodium bicarbonate (30 mL), water (20 mL), and brine (20 mL). The organic portion was dried over sodium sulfate, evaporated, and chromatographed on 70–230 mesh silica gel using methylene chloride to elute the desired diastereomer, (2S, 3S)-2-hydroxy-3-(4-methoxyphenyl)-3-(2-aminophenylthio)-propionic acid, (−)-8′-phenylmenthyl ester (2.10 g, 73% yield from p-anisaldehyde and 4% ethyl acetate in methylene chloride to elute the undesired diastereomer (0.70 g, 24% yield from p-anisaldehyde). The diastereomeric excess was determined to be 50% based upon the 3:1 ratio of desired to undesired product.

EXAMPLE 3

Room Temperature Hydrolysis

To the (2S, 3S)-configured product from Example 2 (2.17 g, 4.08 mmol) was added a methanolic solution of KOH (13.5 mL, 1.51M) and 2 mL of water. Ten mL of methanol were added to enhance the solubility of the material and the mixture was stirred at room temperature. After 2½ days, the solvents were evaporated. The residue was dissolved in water (40 mL), adjusted to pH 7 with 1M HCl, and washed with toluene (2×50 mL). The solution was adjusted to pH 3 with 1M HCl, extracted with chloroform (3×50 mL), dried over sodium sulfate, filtered, and evaporated to yield 0.88 g (68%) of (2S, 3S)-2-hydroxy-3-(4-methoxyphenyl)-3-(2-aminophenylthio)-propionic acid.

EXAMPLE 4

Thiazepinone Synthesis

The final desired ((2S, 3S)-configured) product from Example 1 (0.81 g) was treated with KOH (0.86 g, 15.2 mmol in 2 mL water), and sufficient methanol was added to homogenize the mixture. After 2 hours, the reaction had proceeded to an extent of approximately 50%, and was left to stir overnight. After 24 hours, the solution was concentrated, water (20 mL) was added, the mixture was extracted with methylene chloride (2×30 mL), acidified to pH 2 with 1M HCl, extracted with ethyl acetate (5×30 mL), dried over magnesium sulfate/sodium sulfate, filtered, and evaporated. The product (0.35 g, 1.10 mmol) was dissolved in xylene (5 mL) and heated at reflux overnight.

The mixture was cooled, diluted with hexane (20 mL), and filtered. A portion of the solid was recrystallized from methylene chloride/hexane to yield 180 mg of thiazepinone.

$[\alpha]^{25} = +110°$ (C=1.1, CM$_2$Cl$_2$), +111° (C=0.34 ethanol) M.P.=205° C. Values reported in Inoue et al., (citation, JP No. 78018038, June, 1987: $[\alpha]^{26}$ 129° (C=0.686, ethanol) m.p. 196°–198° C. NMR (CDCl): 8.09 ppm (HL, br s); 7.69–6.75 (8M, M); 5.07 (1M, d); 4.47(dd, 1M); 3.75 (dd, 1M); 3.00 (d, 1M).

This demonstrates the correctness of naming the configuration of the 2-hydroxy-3-(4-methoxyphenyl)-3-(2-aminophenylthio)propionic acid, 8′-phenylmenthyl ester.

EPILOGUE

The present invention is thus provided. Various modifications can be effected by those skilled in the art within the spirit of this invention, the scope of which is particularly pointed out by the following distinctly claimed subject matter.

What is claimed is:

1. A (2*, 3*)-2-hydroxy-3-(4-methoxyphenyl)-3-(2-aminophenylthio)-propionic acid, (*)-8′-phenylmenthyl ester.

2. The ester of claim 1, wherein its configuration is (2S, 3S) and (−), respectively.

* * * * *